United States Patent [19]

DeLuca et al.

[11] Patent Number: 5,104,864
[45] Date of Patent: Apr. 14, 1992

[54] METHOD FOR TREATING AND PREVENTING LOSS OF BONE MASS

[75] Inventors: Hector F. DeLuca, Deerfield; Charles W. Bishop, Verona; Richard B. Mazess, Madison, all of Wis.; John C. Gallagher, Omaha, Nebr.

[73] Assignee: Bone Care International, Inc., Madison, Wis.

[21] Appl. No.: 569,412

[22] Filed: Aug. 17, 1990

Related U.S. Application Data

[63] Continuation of Ser. No. 277,371, Aug. 2, 1988, abandoned.

[51] Int. Cl.$^5$ ....................... A01N 45/00; C07J 172/00
[52] U.S. Cl. ...................................... 514/167; 552/653
[58] Field of Search .............................. 514/167, 141

[56] References Cited

U.S. PATENT DOCUMENTS 4,225,596  9/1980  DeLuca ............................. 514/167
4,588,716  5/1986  DeLuca ............................. 424/90

OTHER PUBLICATIONS

Sjoden et al: "Effects of OHD$_2$ Bone Tissue"; Acta. Endocrinol. (Copenh.) vol. 16, Nr. 4, Aug. 1984, pp. 564–568.
Sjoden et al: Proc. Soc. Exp. Biol Med. 178:432–436 (1985).
Foles, et al., "Long Term Treatment with 1α(OH)D$_3$ for Postmenopausal Osteoporosis: Efficacy and Safety", Osteoporosis 1987-2, C. Christianson, J. S. Johansen, R. J. Rüs (eds.), Osteopress ApS, Copenhagen (1987), pp. 971–973.
Lam et al., "1α-hydroxy Vitamin D$_2$: A Potent Synthetic Analog of Vitamin D$_2$," Science, vol. 186, Nr. 4168, 1974, pp. 1038–1040.
Reeve, L. E., et al., "Biological Activity of α-hydroxy Vitamin D$_2$ in the Rat," Arch. Biochem. Biophys. vol. 186, Nr. 1, Feb. 1978, pp. 164–167.
Sjoden, et al., J. Nutr. 114:2043–2046 (1984).
Physician's Desk Reference, Edition 43, pp. 1746–1748 (1988).
Tanaka, Y., et al., Endocrinology. 1973; 92:417–422.
Sorensen, O. H., et al., Clin. Endocrinol. 1977; 7:169s–175 s.
Hoikka V., et al., Acta. Med. Scand. 1980; 207:221–224.
Shiraki, M., Endocrinol. Japon. 1985; 32:305–315.
Aloia, J. et al., Amer. J. Med. 1988; 84:401–408.
Brown, et al., Lancet 1984; 1:1091–1093.
Podenphant, J., et al., Acta. Med. Scand. 1985; 218:329–333.
Caniggia, et al., Calcif. Tissue Int. 1986; 38:328–332.
Duda, et al., J. Clin. Invest. 1987; 79:1249–1253.
Zerwekh, et al., J. Clin. Endocrinol. Metabol. 1985; 60:615–617.
Horst, et al., Anal. Biochem. 1981; 116:189–203.
Horst, et al., Biochem. J. 1982; 204:185–189.
Sommerfeldt, et al., J. Nutr. 1983; 113:2595–2600.
Brautbar, N., Nephron. 1986; 44:161–166.

Primary Examiner—Frederick E. Waddell
Assistant Examiner—T. J. Criares
Attorney, Agent, or Firm—Carl E. Gulbrandsen

[57] ABSTRACT

A method for reversing loss of bone mass or bone mineral content in a human being suffering from osteoporosis is disclosed which comprises administering to the human being a daily dosage of at least 2.0 micrograms/day of 1-alpha-hydroxy-Vitamin D$_2$.

15 Claims, No Drawings

METHOD FOR TREATING AND PREVENTING LOSS OF BONE MASS

This is a continuation of copending application Ser. No. 07/277,371 filed on Aug. 2, 1988, now abandoned.

TECHNICAL FIELD

This invention relates to a method for treating and preventing metabolic bone disorders characterized by loss of bone mass or by disproportionately low bone mineral content.

More specifically, this invention relates to a method for treating or preventing various known forms of osteoporosis, e.g. postmenopausal, senile and steroid-induced osteoporosis or other disease states one of the characteristics of which is the loss of bone mass or decreased mineral content.

Still more specifically, this invention relates to a method for treating or for preventing the depletion of bone of women who are entering menopause or who are postmenopausal.

BACKGROUND OF THE INVENTION

Numerous metabolic bone disorders are known to the medical community which are characterized by loss of bone mass or disproportionate mineralization of bone. These disorders include postmenopausal osteoporosis, senile osteoporosis, renal osteodystrophy, corticosteroid-induced osteopenia, and anticonvulsant osteomalacia. Of these disorders, postmenopausal and senile osteoporosis are most commonly encountered in normal medical practice.

As a group, these bone depletive disorders are a major and growing public health problem in the United States. Together, they cause more than 1 million bone fractures per year, primarily of the spine, hip, and distal forearm, and result in an annual cost of $6 or 7 billion to the American society. Unfortunately, the incidence of these bone disorders will rise significantly as the mean age of the U.S. population continues to increase.

Despite differing etiologies, the aforementioned metabolic bone disorders develop during an extended period of negative calcium balance. This commonality of the disorders suggests that agents which stimulate intestinal calcium absorption may be effective in restoring calcium balance and thereby treating or preventing the development of such bone disorders. It has long been known that Vitamin D plays a critical role in stimulating calcium absorption and regulating calcium metabolism. The discovery of the active forms of Vitamin D, [M. F. Holick et al., Proc. Natl. Acad. Sci. USA 68, 803–804 (1971); G. Jones et al., Biochemistry 14, 1250–1256 (1975)] and active Vitamin D analogues [M. F. Holick et al., Science 180, 190–191 (1973); H. Y. Lam et al., Science 186, 1038–1040 (1974)], caused much excitement and speculation about the usefulness of these compounds in the treatment of bone depletive disorders.

Animal studies examining the effects of these active Vitamin D compounds suggested that such agents would be useful in restoring calcium balance. Further, an early clinical study indicated that administration of 0.5 µg/day of 1,25-dihydroxycholecalciferol (1,25 Vitamin $D_3$) to a group of postmenopausal women improved the intestinal calcium absorption as well as the calcium balance of these women. On this basis, U.S. Pat. No. 4,225,596 ("'596 Patent") described and claimed the use of 1,25 Vitamin $D_3$ for increasing calcium absorption and retention. Such use also was claimed in the same patent for 1,25 dihydroxyergocalciferol (1,25 Vitamin $D_2$) and 1α-hydroxyergocalciferol (1α-Vitamin $D_2$), which the patent teaches are "eminently suitable and readily substitutable for the 1,25 dihydroxycholecalciferol."

The best indicator of the efficacy of Vitamin D compounds to prevent or treat depletive bone disorders is bone itself rather than calcium absorption or calcium balance. More recent clinical data indicates that at the dosage ranges taught in the '596 Patent, 1,25 Vitamin $D_3$ has, at best, modest efficacy in preventing or restoring loss of bone mass or bone mineral content [S. M. Ott and C. H. Chesnut, In: J. Jensen et al., eds., Norhaven A/S, Viborg, p. 83 (1987); J. C. Gallagher et al., 7th Workshop on Vitamin D, Rancho Mirage, p. 196 (1988); J. Aloia et al., Amer. J. Med. 84:401–408 (1988)].

Together these clinical studies with 1,25 Vitamin $D_3$, and one other conducted with 1α-Vitamin $D_3$ [M. Shiraki et al., Endocrinol. Japan 32,305–315 (1985)], indicate that the ability of these agents to restore lost bone mass or bone mineral content is dose related. These studies also indicate, however, that at the dosage ranges required for the agents to be truly effective, toxicity in the form of hypercalcemia and hypercalciuria becomes a major problem. Thus, attempts to increase the amount of 1,25 Vitamin $D_3$ above 0.5 µg/day have frequently resulted in toxicity. At dosage levels below 0.5 µg/day no effects are observed on bone. [See G. F. Jensen et al., Clin. Endocrinol. 16, 515–524 (1982); C. Christiansen et al., Eur. J. Clin. Invest. 11, 305–309 (1981)]. Two µg/day of 1α-Vitamin $D_3$ was found to have efficacy in increasing bone mass in patients exhibiting senile osteoporosis [O. H. Sorensen et al., Clin. Endocrinol. 7, 169S–175S (1977)]. Data from the clinical studies in Japan, a population that has low calcium intake, indicate that efficacy is found with 1α-Vitamin $D_3$ when administered at 1 µg/day [M..Shiraki et al., Endocrinol. Japan. 32:305–315 (1985); H. Orimo et al., Bone and Mineral 3, 47–52 (1987)]. At 2 µg/day, however, toxicity with 1α-Vitamin $D_3$ occurs in approximately 67 percent of the patients, and at 1 µg/day this percentage is approximately 20 percent.

Thus, the prior art teaches that due to their toxicity, 1 hydroxylated Vitamin D compounds can only be administered at dosages that are, at best, modestly beneficial in preventing or treating loss of bone or bone mineral content. Indeed, Aloia recommends that alternative routes of administration be sought which might avoid the toxicity problems and allow higher dosage levels to be achieved. [J. Aloia et al , Amer. J. Med. 84:401–408 (1988)].

SUMMARY OF THE INVENTION

The present invention discloses a method whereby the bone forming activity of 1-hydroxylated Vitamin D compounds is made available to safely prevent or treat bone depletive disorders. With the exception of the data provided herein, no clinical data are available with respect to the 1-hydroxylated Vitamin $D_2$ compound. Nonetheless, in the prior art, such compounds have been considered as essentially equivalent to their Vitamin $D_3$ counterparts. Thus, when the prior art teaches that because of its extreme toxicity 1α-Vitamin $D_3$ may not be safely administered at normal calcium intakes in excess of 2 µg/day, a person skilled in the art would understand that the same warning also applies to 1α-Vitamin D$_2$.

During the course of prior investigations, a comparison has been made between 1α-Vitamin D$_2$ and 1α-Vitamin D$_3$. 1α-Vitamin D$_2$ is equally active as 1α-Vitamin D$_3$ in the healing of rickets, the stimulation of intestinal calcium absorption and in the elevation of serum inorganic phosphorous of rachitic rats. [G. Sjoden et al., J. Nutr. 114, 2043-2046 (1984)]. In the same laboratory animal it has also been found that, 1α-Vitamin D$_2$ is 5 to 15 times less toxic than 1α-Vitamin D$_3$. [G. Sjoden et al., Proc. Soc. Exp. Biol. Med. 178, 432-436 (1985)].

It has now been found that 1α-Vitamin D$_2$ may be safely administered to human subjects experiencing or having a tendency toward loss of bone mass or bone mineral content at dosages greater than 3 μg/day.

These findings indicate that compounds of the formula (I):

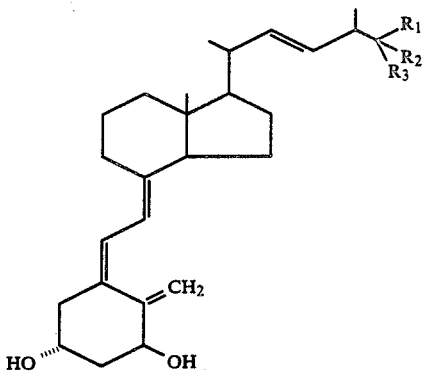

where R$_1$, R$_2$, R$_3$, are each selected from the group consisting of hydrogen, hydroxyl, lower alkyl, acyl, O-alkyl, and have the novel attribute of being substantially less toxic than their Vitamin D$_3$ counterparts when administered to subjects experiencing or having a tendency toward loss of bone mass or bone mineral content. This novel attribute permits administration of the compounds of formula I at dosage levels higher than possible with the Vitamin D$_3$ compounds thus providing greater efficacy than heretofore possible in preventing or restoring such loss of bone mass or bone mineral content.

The present invention is intended to be used in all bone depletive disorders which respond to administration of active forms of Vitamin D, including renal osteodystrophy, anticonvulsant osteomalacia, hypophosphatemic Vitamin D-resistant rickets, pseudo-deficiency (Vitamin D-dependent) rickets, nutritional and malabsorptive rickets, osteomalacia and osteopenias secondary to hypoparathyroidism, post-surgical hypoparathyroidism, idiopathic hypoparathyroidism, pseudoparathyroidism and alcoholism.

The present invention also is intended to be used in those bone depletive disorders classified as osteoporosis, particularly post-menopausal osteoporosis, senile osteoporosis, idiopathic osteoporosis, immobilization osteoporosis, post-lactational osteoporosis, glucocorticoid, alcohol or drug-induced osteoporosis, juvenile osteoporosis, osteoporosis secondary to gonadal insufficiency, malnutrition, hyperprolactinemia, or disorders of the gastrointestinal tract, liver, or kidneys, and osteoporosis that is a sequella of prior osteomalacia, chronic disorders involving the bone marrow, and heritable forms of osteoporosis such as osteoporosis imperfecta and its variants, and other heritable disorders of connective tissue.

EXAMPLE 1

Six postmenopausal osteoporotic women were enrolled in an open label study. The selected patients had ages between 55 and 75 years, and exhibited L2-L3 vertebral bone mineral density between 0.7 and 1.05 g/cm$^2$, as determined by measurements with a LUNAR Radiation dual photon absorptiometer. (The mean bone mineral density in women with osteoporosis is about 0.85±0.17 g/cm$^2$, so that these limits correspond to about the 15th to the 85th percentiles.)

On admission to the study, all patients received instruction on selecting a daily diet containing 400 to 600 mg. of calcium. Compliance to this diet was verified at weekly intervals by 24-hour food records and by interviews with each patient.

All patients completed a one-week baseline period, a five-week treatment period, and a one-week post-treatment observation period. During the treatment period, patients orally self-administered 1α-Vitamin D$_2$ at an initial dose of 0.5 μg/day for the first week, and at successively higher doses of 1.0, 2.0, 4.0 and 5.0 μg/day in each of the following four weeks. All doses were administered before breakfast.

Blood and urine chemistries were monitored on a weekly basis throughout the study. Key blood chemistries included fasting serum levels of calcium, phosphorus, osteocalcin, creatinine and blood urea nitrogen. Key urine chemistries included 24-hour excretion of calcium, phosphorus and creatinine.

Data from the study clearly demonstrated that 1α-Vitamin D$_2$ can be safely administered at high dose levels. As shown in Table 1, all six patients tolerated a 4.0 μg/day dose of this compound without exhibiting hypercalciuria (>350 mg/24 hr) or hypercalcemia (>11.0 mg/dL). Five of the patients tolerated a 5.0 μg/day dosage without side effects, while the sixth patient showed a mild hypercalciuria, without attendant hypercalcemia, at this dosage.

TABLE 1

Dose-response relationship between orally administered 1α-Vitamin D$_2$ and fasting serum and 24-hour urinary calcium values in postmenopausal osteoporotic patients.

| Dose | Fasting Serum Ca | | 24-hr Urinary Ca | |
|---|---|---|---|---|
| | Mean ± SE | Range | Mean ± SE | Range |
| 0.5 μg/d | 9.80 ± 0.10 | (9.51–10.20) | 121.8 ± 17.2 | (55.3–180.0) |
| 1.0 μg/d | 9.81 ± 0.08 | (9.61–10.18) | 132.2 ± 16.7 | (67.8–187.1) |
| 2.0 μg/d | 9.87 ± 0.15 | (9.58–10.56) | 169.9 ± 16.4 | (110.5–215.1) |
| 4.0 μg/d | 9.92 ± 0.10 | (9.65–10.33) | 193.9 ± 30.1 | (133.8–324.1) |
| 5.0 μg/d | 9.80 ± 0.09 | (9.61–10.15) | 221.3 ± 37.0 | (149.9–405.9) |

Additional blood and urine data from this clinical study supported the conclusion that 1α-Vitamin D$_2$ can be safely administered at high dosages. In particular, this compound did not adversely affect kidney function, as determined by creatinine clearance and blood levels of urea nitrogen; nor did it increase urinary excretion of hydroxyproline, indicating the absence of any stimulatory effect on bone resorption. The compound had no effect on any routinely monitored serum parameters, indicating the absence of adverse metabolic effects.

A positive effect of 1α-Vitamin D$_2$ on calcium homeostasis was evident from modest increases in 24-hour urinary calcium levels (see Table 1), confirming that the compound increases intestinal calcium absorption.

EXAMPLE 2

A clinical study is conducted with postmenopausal osteoporotic out-patients having ages between 55 and 75 years. The study involves up to 120 patients randomly divided into three treatment groups, and continues for 12 to 18 months. Two of the treatment groups receive constant dosages of 1α-Vitamin $D_2$ (u.i.d.; two different dose levels above 3.0 μg/day) and the other group receives a matching placebo. All patients maintain a normal intake of dietary calcium (500 to 800 mg/day) and refrain from using calcium supplements. Efficacy is evaluated by pre- and post-treatment comparisons of the patient groups with regard to (a) total body calcium retention, (b) radial and spinal bone mineral density as determined by dual-photon absorptiometry (DPA) or dual-energy x-ray absorptiometry (DEXA), (c) bone biopsies of the iliac crest, and (d) determinations of serum osteocalcin. Safety is evaluated by comparisons of urinary hydroxyproline excretion, serum and urine calcium levels, creatinine clearance, blood urea nitrogen, and other routine determinations.

The results show that patients treated with 1α-Vitamin $D_2$ exhibit significantly higher total body calcium, and radial and spinal bone densities relative to patients treated with placebo. The treated patients also exhibit significant elevations in serum osteocalcin. Bone biopsies obtained from the treated patients show that 1α-Vitamin $D_2$ stimulates normal bone formation. The monitored safety parameters confirm an insignificant incidence of hypercalcemia or hypercalciuria, or any other metabolic disturbance with 1α-Vitamin $D_2$ therapy.

EXAMPLE 3

A clinical study is conducted with healthy postmenopausal women having ages between 55 and 60 years. The study involves up to 80 patients randomly divided into two treatment groups, and continues for 12 to 18 months. One treatment group receives a constant dosage of 1α-Vitamin $D_2$ (u.i.d.; a dose level above 3.0 μg/day) and the other receives a matching placebo. The study is conducted as indicated in Example 2 above.

The results show that patients treated with 1α-Vitamin $D_2$ exhibit reduced losses in total body calcium, radial or spinal bone densities relative to baseline values. In contrast, patients treated with placebo show significant losses in these parameters relative to baseline values. The monitored safety parameters confirm the safety of long-term 1α-Vitamin $D_2$ administration at this dose level.

EXAMPLE 4

A twelve month double-blind placebo-controlled clinical trial is conducted with thirty men and women with renal disease who are undergoing chronic hemodialysis. All patients enter an 8-week control period during which time they receive a maintenance dose of Vitamin $D_3$ (400 IU/day). After this control period, the patients are randomized into two treatment groups: one group receives a constant dosage of 1α-Vitamin $D_2$ (u.i.d.; a dosage greater than 3.0 μg/day) and the other group receives a matching placebo. Both treatment groups receive a maintenance dosage of Vitamin $D_3$, maintain a normal intake of dietary calcium, and refrain from using calcium supplements. Efficacy is evaluated by pre- and post-treatment comparisons of the two patient groups with regard to (a) direct measurements of intestinal calcium absorption, (b) total body calcium retention, (c) radial and spinal bone mineral density, and (d) determinations of serum calcium and osteocalcin. Safety is evaluated by regular monitoring of serum calcium.

Analysis of the clinical data show that 1α-Vitamin $D_2$ significantly increases serum osteocalcin levels and intestinal calcium absorption, as determined by direct measurements using a double-isotope technique. Patients treated with this compound show normalized serum calcium levels, stable values for total body calcium, and stable radial and spinal bone densities relative to baseline values. In contrast, patients treated with placebo show frequent hypocalcemia, significant reductions in total body calcium and radial and spinal bone density. An insignificant incidence of hypercalcemia is observed in the treated group.

The foregoing examples demonstrate that 1α-Vitamin $D_2$ is effective in preventing or restoring the loss of bone mass or bone mineral content while being substantially less toxic than 1α-Vitamin $D_3$. It is to be understood that although the foregoing examples detail the use of 1α-Vitamin $D_2$, other compounds within the scope of the claims may be readily utilized in the treatment of this invention with essentially equivalent results. For example, 1,25 Vitamin $D_2$ shows activity equivalent to 1,25-Vitamin $D_3$ and is also significantly less toxic than its Vitamin $D_3$ counterpart. Also included within the scope of claims would be administration of effective dosages of the compound of formula I in conjunction with administration of other Vitamin D compounds, hormones or other agents which have been shown to stimulate bone formulation in subjects experiencing or tending toward loss of bone mass or bone mineral content.

Such other Vitamin D compounds would include Vitamin D, 25OH Vitamin D, 1,25 Vitamin $D_3$, 1α-Vitamin $D_3$ and chemical variations which retain the characteristics of these Vitamin D compounds and are contemplated as equivalents.

Such hormones or other agents would include conjugated estrogens or their equivalents, calcitonin, biphosphonates, calcium supplements, cobalamin, pertussis toxin and boron. Possible dose ranges for these co-administered agents are provided in Table 2.

TABLE 2

POSSIBLE ORAL DOSE RANGES FOR VARIOUS AGENTS CO-ADMINISTERED WITH 1α-HYDROXY-VITAMIN $D_2$ AND 1,25-DIHYDROXYVITAMIN $D_2$

| AGENT | DOSE RANGES | | |
|---|---|---|---|
| | Broad | Preferred | Most Preferred |
| Conjugated Estrogens or equivalent (mg/day) | 0.3–5.0 | 0.4–2.4 | 0.6–1.2 |
| Sodium Fluoride (mg/day) | 5–150 | 30–75 | 40–60 |
| Calcitonin (IU/day) | 5–800 | 25–500 | 50–200 |
| Biphosphonates (mg/day) | 50–2000 | 100–1500 | 250–1000 |
| Calcium Supplements (mg/day) | 250–2500 | 500–1500 | 750–1000 |
| Cobalamin (μg/day) | 5–200 | 20–100 | 30–50 |
| Pertussis Toxin | 0.1–2000 | 10–1500 | 100–1000 |

TABLE 2-continued

POSSIBLE ORAL DOSE RANGES FOR VARIOUS AGENTS CO-ADMINISTERED WITH 1α-HYDROXY-VITAMIN $D_2$ AND 1,25-DIHYDROXYVITAMIN $D_2$

| AGENT | DOSE RANGES | | |
|---|---|---|---|
| | Broad | Preferred | Most Preferred |
| (mg/day) Boron (mg/day) | 0.10–3000 | 1–250 | 2–100 |

Although the examples detail dosage by mouth, it is to be understood that the compounds can be administered in alternative fashions, including intranasally, transdermally, intrarectally, intravaginally, subcutaneously, intravenously, and intramuscularly.

Dosage forms of 1α-Vitamin $D_2$ can be prepared by dissolving or suspending the compound in, or adsorbing it on, non-toxic pharmaceutically acceptable carriers as is well known in the art. Such carriers may be either solid or liquid such as, for example, corn starch, lactose, sucrose, peanut oil, olive oil, neutral oil, and propylene glycol. If a solid carrier is used, the dosage form of the compound may be tablets, capsules, powders, suppositories, or lozenges. If a liquid carrier is used, soft gelatin capsules, transdermal patches, aerosol sprays, topical creams, syrups or liquid suspensions, emulsions or solutions may be the dosage form. The dosage forms may also contain excipients, such as preserving, stabilizing, wetting, emulsifying agents, etc.

Bulk quantities of 1α-Vitamin $D_2$ for the practice of this invention can be readily obtained in accordance with the processes of U.S. Pat. Nos. 3,907,843, 4,195,027, 4,202,829, 4,234,495, 4,260,549, 4,555,364, and 4,554,106.

Having thus described the invention, what we claim is:

1. A method for reversing loss of bone mass or bone mineral content in a human being displaying or predisposed to developing osteoporosis, comprising the step of: administering to said human being an amount of 1α-hydroxyergocalciferol sufficient to reverse loss of bone mass or bone mineral content without causing hypercalciuria or hypercalcemia, said amount being at least 2.0 μg/day.

2. The method according to claim 1 wherein said human being is greater than 45 years of age.

3. The method according to claim 1 wherein said human being is a woman who is hypoestrogenic.

4. The method according to claim 1 wherein the compound is administered to women during or subsequent to menopause.

5. The method according to claim 1 wherein said osteoporosis is post-menopausal osteoporosis.

6. The method according to claim 1 wherein said osteoporosis is senile osteoporosis.

7. The method of claim 1 wherein the compound is administered to women prior to the onset of menopause.

8. The method of claim 1 wherein 1α-hydroxyergocalciferol is administered in an amount greater than 2.0 μg/day.

9. The method of claim 1 wherein 1α-hydroxyergocalciferol is administered in an amount greater than 2.5 μg/day.

10. The method of claim 1 wherein 1α-hydroxyergocalciferol is administered in an amount greater than 3.0 μg/day.

11. The method of claim 1 wherein the 1α-hydroxyergocalciferol, in solution, in a liquid vehicle ingestible by and non-toxic to said human beings is administered orally in encapsulated form.

12. The method of claim 1, wherein said administration of said 1α-hydroxyergocalciferol is parenteral.

13. The method of claim 12, wherein said administration is by subcutaneous, intramuscular, or intraveneous injection, nasopharyngeal or mucosal absorption, or trans-dermal absorption.

14. The method of claim 1 wherein said administration of said 1α-hydroxyergocalciferal is nonparenteral.

15. A method for increasing bone mass by stimulating bone formation in a human being displaying post-menopausal or senile osteoporosis, said method comprising the steps of:
   a. maintaining a calcium intake in said human being of between 400 to 800 mg/day;
   b. administering daily to said human being an amount of 1α-hydroxyergocalciferol sufficient to stimulate bone formation without causing hypercalciuria and hypercalcemia, said amount being not less than 2.0 μg/day.

* * * * *